United States Patent
Xie et al.

(10) Patent No.: US 8,658,664 B2
(45) Date of Patent: Feb. 25, 2014

(54) CYCLOPAMINE TARTRATE SALT AND USES THEREOF

(75) Inventors: Jingwu Xie, Westfield, IN (US); Massoud Garrossian, Plano, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 487 days.

(21) Appl. No.: 12/806,271

(22) Filed: Aug. 9, 2010

(65) Prior Publication Data

US 2011/0092530 A1    Apr. 21, 2011

Related U.S. Application Data

(63) Continuation-in-part of application No. PCT/US2009/000737, filed on Feb. 5, 2009.

(60) Provisional application No. 61/027,337, filed on Feb. 8, 2008.

(51) Int. Cl.
 *A61K 31/44* (2006.01)

(52) U.S. Cl.
 USPC .......................................................... 514/278

(58) Field of Classification Search
 USPC ........................................ 514/179, 278, 110
 See application file for complete search history.

(56) References Cited

U.S. PATENT DOCUMENTS

| 3,046,301 A * | 7/1962 | Phillips et al. ................... 560/19 |
| 5,855,916 A | 1/1999 | Chiesi et al. ................... 424/488 |
| 7,893,078 B2 * | 2/2011 | Tas et al. ....................... 514/278 |
| 8,017,648 B2 * | 9/2011 | Castro et al. ................... 514/455 |
| 2004/0072914 A1 | 4/2004 | Tas et al. ....................... 514/659 |

* cited by examiner

*Primary Examiner* — Kevin E Weddington

(57) ABSTRACT

The present invention provides compositions and methods for modulating smoothened-dependent pathway activation. The present invention provides highly water-soluble analogs of cyclopamine that are potent, hedgehog signaling inhibitors less toxic than cyclopamine. The compounds of the present invention are particularly useful in treating cancers associated with hedgehog signalling.

5 Claims, 7 Drawing Sheets

CYCLOPAMINE TARTRATE SALT AND USES THEREOF

CROSS REFERENCE TO RELATED APPLICATION

This continuation-in-part application claims benefit of priority under 35 U.S.C. §120 of international application PCT/US2009/000737, filed Feb. 5, 2009, which claims benefit of priority under 35 U.S.C. §119(e) of Provisional Patent Application U.S. Ser. No. 61/027,337 filed on Feb. 8, 2008, now abandoned, the entirety of both of which is incorporated by reference.

FEDERAL FUNDING LEGEND

This invention was produced in part using funds obtained through grant CA94160 from the National Cancer Institute. Consequently, the federal government has certain rights in this invention.

BACKGROUND OF THE INVENTION

1. Field of the Invention

The present invention relates to novel methods for the treatment of cancer. More specifically, the present invention relates to the inhibition of the hedgehog signaling pathway by the direct binding of a cyclopamine derivative to protein smoothened and uses thereof.

2. Description of the Related Art

The hedgehog (Hh) gene was identified by two Nobel laureates through genetic analysis of segmentation of fruit fly Drosophila (1). The seven transmembrane domain containing protein smoothened (SMO) serves as the key player for signal transduction of this pathway, whose function is inhibited by another transmembrane protein Patched (PTC) in the absence of hedgehog ligands. In the presence of active hedgehog ligands, binding of hedgehog to its receptor PTC releases this inhibition, allowing SMO to signal downstream, eventually to Gli transcription factors. As transcription factors, Gli molecules can regulate target gene expression by direct association with a specific consensus sequence located in the promoter region of the target genes (2,3).

The hedgehog signaling pathway is critical for stem cell functions and development of cancer. The major breakthrough in contemporary understanding of hedgehog signaling in human cancers came from the discovery that mutations of human homologue of the drosophila patched gene (PTCH1) are associated with a rare hereditary form of basal cell carcinoma (BCC)— Basal Cell Nevus Syndrome (also called Gorlin syndrome) (4-6). Recent studies indicate that Hh signaling is activated in many types of extracutaneous tumors, including brain tumors, gastrointestinal, prostate, lung and breast cancers (7). Specific signaling antagonists for the hedgehog pathway have been discovered and synthesized with significant clinical implications in novel cancer therapeutics. The successful phase I clinical trial with a hedgehog antagonist by Genentech further highlights the feasibility and clinical implications of inhibiting hedgehog signaling for cancer treatment.

Cyclopamine is shown to act through direct binding of smoothened (8). After the discoveries of connections between cyclopamine, the activity of hedgehog signaling pathway and cancer formation, scientists have directed efforts towards studies employing cyclopamine as the compound to inhibit the hedgehog pathway and offer potential cure for cancers. Several interesting findings have reported the effect of cyclopamine against various cancers (7). However, there are several issues associated with cyclopamine. Firstly, cyclopamine is not water-soluble which creates problems in drug delivery. Secondly, cyclopamine is toxic, causing off-target effects.

There is a need in the art for a cyclopamine derivative that is water-soluble, possesses low toxicity and is a potent inhibitor of the hedgehog pathway. The present invention fulfills this longstanding need in the art.

SUMMARY OF THE INVENTION

The present invention provides water-soluble hydroxy carboxylic salts of steroidal alkaloid cyclopamine that are considerably less toxic than cyclopamine, and useful for inhibiting proliferation of cells and/or promoting apoptosis in a cell, such as in the treatment of proliferative disorders associated with the hedgehog signaling pathway including psoriasis, and cancers. The hedgehog pathway antagonists of the present invention may be used to inhibit proliferation (or other biological consequences) of cells or tissues.

In certain embodiments, the present methods are used to counteract the phenotypic effects of unwanted activation of a Hedgehog pathway, such as resulting from hedgehog gain-of-function, Ptc loss-of-function or Smo gain-of-function mutations. For instance, the present methods can involve contacting a cell (in vitro or in vivo) with a hedgehog pathway antagonist of the present invention (defined below) in an amount sufficient to antagonize Smo-dependent pathway activation. Such antagonism will stop or slow unwanted cell proliferation and can lead to cell death.

In certain embodiments, the methods and compounds of the present invention may be used to prevent or treat stem cell related human conditions by administering to the subject in need thereof an effective amount of the hydroxy carboxylic salt of cyclopamine.

In certain embodiments, the methods and compounds of the present invention may be used to regulate proliferation of cells and/or cell death in vitro and/or in vivo such as in the treatment of cell proliferative diseases associated with hedgehog signaling including psoriasis, basal cell carcinoma and malignant disorders of the head, neck, nasal cavity, paranasal sinuses, nasopharynx, oral cavity, oropharynx, larynx, hypopharynx, salivary glands, paragangliomas, pancreas, stomach, skin, esophagus, liver and biliary tree, bone, intestine, colon, rectum, ovaries, prostate, lung, breast, lymphatic system, blood, bone marrow central nervous system, or brain.

Certain embodiments of this invention are methods of treating cell proliferative diseases associated with hedgehog signalling in a subject, comprising contacting the cell with an effective amount of a water-soluble hydroxy carboxylic salt of cyclopamine. Hydroxy carboxylic salts of cyclopamine are water-soluble, less toxic compared to cyclopamine, and represented by the formula:

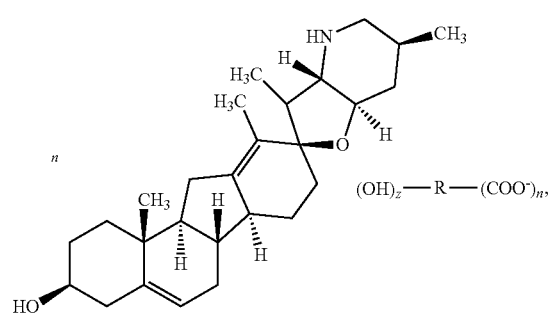

In certain embodiments, methods of the present invention may be used for treating psoriasis, primary cancer, metastasized cancer or other cell proliferative diseases associated with hedgehog signaling, in a subject, comprising contacting the cell with an effective amount of cyclopamine tartrate of formula:

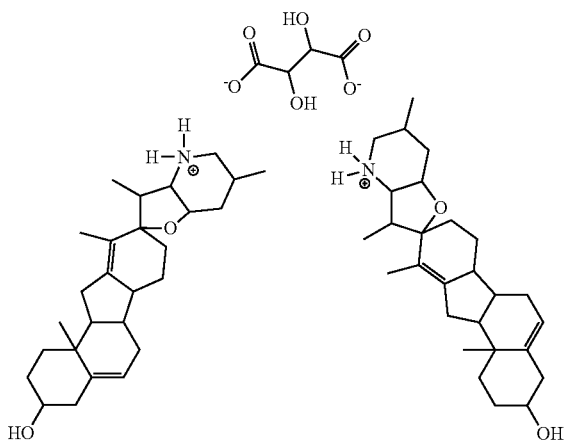

In certain embodiments, the methods of the present invention may be used for treating a cancer associated with hedgehog signaling in a subject by administering to said subject a therapeutically effective amount of cyclopamine tartrate of above formula, or analogues thereof. In certain other embodiments, the methods of the present invention may be used for reducing in a subject, the incidence of metastasis of a cancer associated with hedgehog signaling, said method comprising administering to said subject a therapeutically effective amount of a water-soluble hydroxy carboxylic salt of cyclopamine which is less toxic than cyclopamine, such as cyclopamine tartrate.

In certain embodiments, the method of the instant invention may be used for antagonizing the hedgehog pathway in a cell, comprising contacting a cell expressing smoothened with an effective amount of water-soluble hydroxy carboxylic salt of cyclopamine which is less toxic than cyclopamine, such as cyclopamine tartrate or analogues thereof.

In certain embodiments, the methods and compounds of the present invention may be used to treat the symptoms of psoriasis in a subject. The compounds of the present invention may be used to treat psoriasis as a single agent or in combination with one or more anti-psoriasis agents. In particular embodiments, the compounds of the present invention are topically administered to a subject in need thereof.

In one preferred embodiment, the present invention provides a method of treating a skin tumor in a subject, comprising administering to said subject a therapeutically effective amount of cyclopamine tartrate or analogues thereof, wherein said administration results in the shrinkage of tumors on the skin.

Another embodiment of the present invention is directed to a method of reducing the incidence of pancreatic cancer metastasis, said method comprising administering to a subject in need thereof a therapeutically effective amount of cyclopamine tartrate or analogues thereof, wherein said administration reducing the incidence of pancreatic cancer metastasis.

The compounds of the present invention may be further formulated as a pharmaceutical preparation comprising a pharmaceutically acceptable excipient, for administration to a patient as a means of treating cancer. The hedgehog pathway antagonists or analogues thereof, of the present invention and/or preparations comprising them may be administered to a patient to treat conditions involving unwanted cell proliferation, e.g., cancer and/or tumors of the head, neck, nasal cavity, paranasal sinuses, nasopharynx, oral cavity, oropharynx, larynx, hypopharynx, salivary glands, paragangliomas, pancreas, stomach, skin, esophagus, liver and biliary tree, bone, intestine, colon, rectum, ovaries, prostate, lung, breast, lymphatic system, blood, bone marrow central nervous system, or brain. In certain embodiments, such compounds or preparations are administered systemically, e.g., parenterally and/or locally, e.g., topically.

BRIEF DESCRIPTION OF THE DRAWINGS

FIG. 6A shows a simplified schematic diagram of Motor Neuron differentiation. FIG. 6B is a gel shift assay monitoring H9: a marker for motor neuron differentiation. FIG. 6C shows fluorescent microscopy in presence of 4′,6-diamidino-2-phenylindole indicating Cyc-T reduces the number and the size of EBs. FIG. 6D shows that Cyc-T reduces the number and the size of EBs.

DETAILED DESCRIPTION OF THE INVENTION

Figure 1:
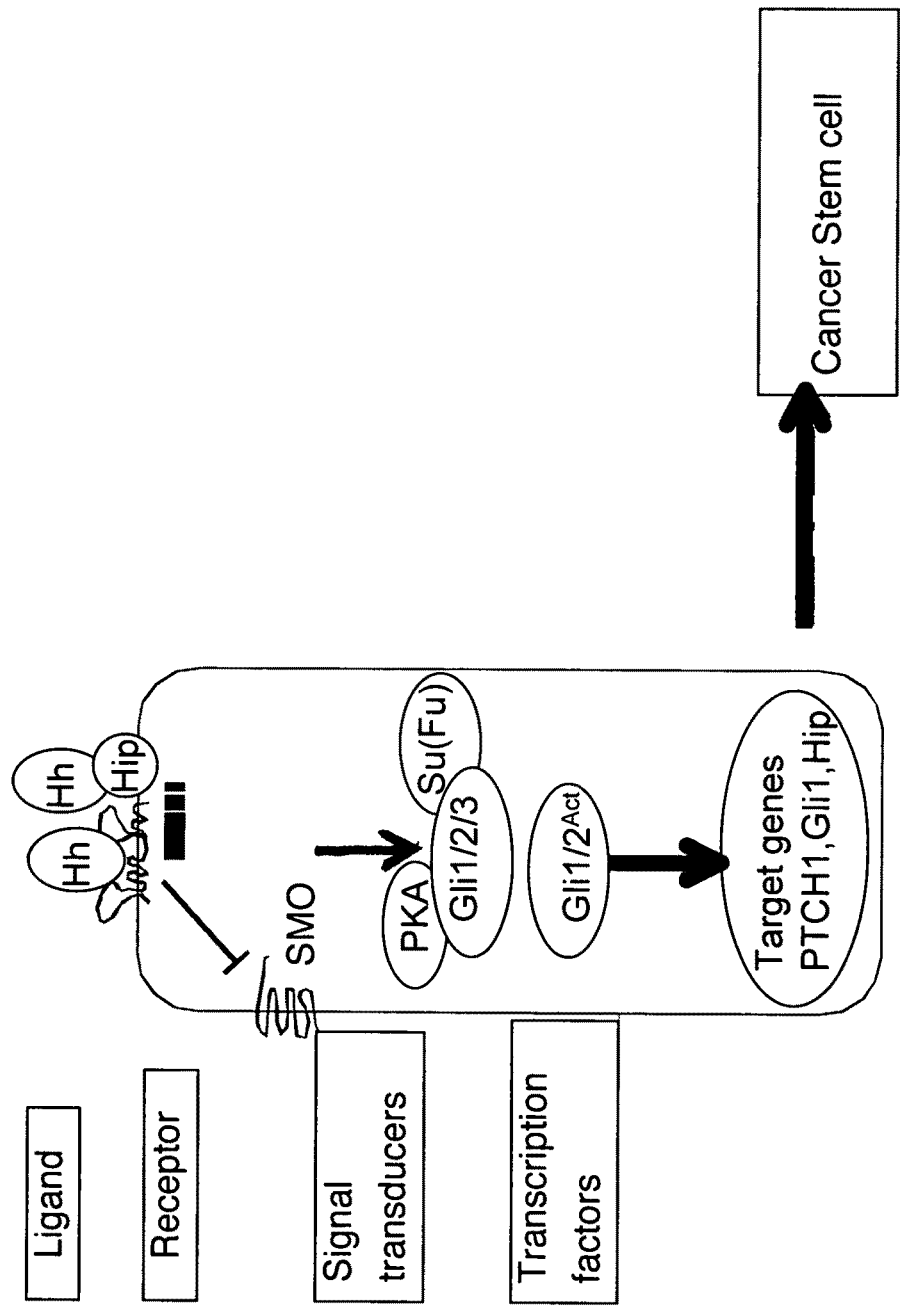
FIG. 1 shows a simplified schematic diagram of hedgehog signaling.

As used herein the specification, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. Furthermore, unless otherwise required by context, singular terms shall include pluralities and plural terms shall include the singular.

As used herein, the term "or" in the claims is used to mean "and/or" unless explicitly indicated to refer to alternatives only or the alternatives are mutually exclusive, although the disclosure supports a definition that refers to only alternatives and "and/or."

The term "hydroxy carboxylic acid" refers to organic acids of general formula R—COOH, characterized by the presence of a carboxyl group (—COOH), and a hydroxyl group (—OH).

"Hydroxy carboxylic salt" of cyclopamine is the product formed from the neutralization reaction of the base-cyclopamine and a hydroxy carboxylic acid. Hydroxy carboxylic salts of cyclopamine are of the formula:

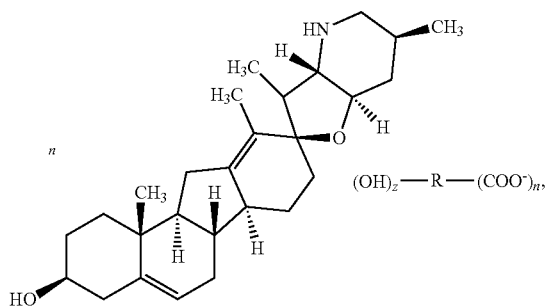

As used herein, the term primary cancer refers to the original site (organ or tissue) where a cancer originates. Exemplary primary cancers may be located in the head, neck, nasal cavity, paranasal sinuses, nasopharynx, oral cavity, oropharynx, larynx, hypopharynx, salivary glands, paragangliomas, pancreas, stomach, skin, esophagus, liver and biliary tree, bone, intestine, colon, rectum, ovaries, prostate, lung, breast, lymphatic system, blood, bone marrow central nervous system, or brain.

"Basal cell carcinomas" exist in a variety of clinical and histological forms such as nodular-ulcerative, superficial, pigmented, morphealike, fibroepithelioma and nevoid syndrome. Basal cell carcinomas are the most common cutaneous neoplasms found in humans. The majority of new cases of non-melanoma skin cancers fall into this category.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potential for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements.

Other carcinomatous epithelial growths are "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

An "effective amount" of a subject compound, with respect to the present methods of treatment, refers to an amount of the antagonist in a preparation which, when applied as part of a desired dosage regimen brings about, e.g., a change in the rate of cell proliferation and/or rate of survival of a cell according to clinically acceptable standards for the disorder to be treated.

The terms "epithelia", "epithelial" and "epithelium" refer to the cellular covering of internal and external body surfaces (cutaneous, mucous and serous), including the glands and other structures derived therefrom, e.g., corneal, esophogeal, epidermal, and hair follicle epithelial cells. Other exemplary epithelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, like that which is characteristically found lining hollow organs that are subject to great mechanical change due to contraction and distention, e.g., tissue which represents a transition between stratified squamous and columnar epithelium.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "hedgehog pathway antagonist" refers to an agent that inhibits the function of the hedgehog pathway, e.g., represses transcription of target genes (Gli1 and Ptc genes), which in normal cells are induced by contact of the cell with hedgehog. In addition to altering a smoothened dependent pathway, in certain embodiments the hedgehog pathway antagonists of the current invention can be used to overcome a Ptc loss-of-function, smoothened gain-of-function, and/or a hedgehog gain-of-function. The terms "loss-of-function" and "gain-of-function", as appropriate, refer to an aberrant modification or mutation of, e.g., a Ptc gene, hedgehog gene, or smoothened gene, or a decrease or increase in the level of expression of such a gene, which results in a phenotype, e.g., which resembles contacting a cell with a hedgehog protein, such as aberrant activation of a hedgehog pathway or resemble loss of Smo function. The mutation may include a loss of the ability of the Ptc or Smo gene product (s) to regulate the level of activity of Gli/Ci proteins, e.g., Gli1 Gli2, and Gli3.

As used herein, "immortalized cells" refers to cells that have been altered via chemical and/or recombinant means such that the cells have the ability to grow through an indefinite number of divisions in culture.

A "patient" or "subject" to be treated by the present method can mean either a human or non-human animal.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Certain embodiments of this invention are directed to methods of treating cancer associated with hedgehog signaling in a subject, comprising administering to the subject an effective amount of a water-soluble hydroxy carboxylic salt of cyclopamine which is less toxic than cyclopamine. Hydroxy carboxylic salts of cyclopamine are represented by the formula:

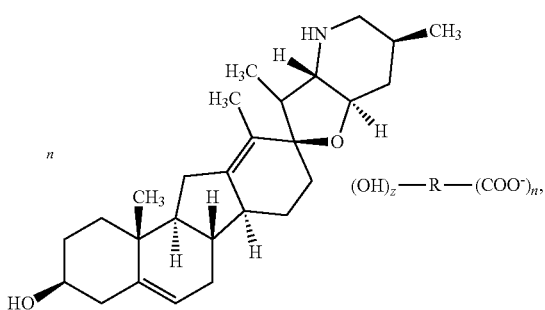

Certain embodiments of this invention are methods of preventing and treating stem cell related human conditions by administering to the subject in need thereof an effective amount of the hydroxy carboxylic salt of cyclopamine.

One embodiment of this invention is a method of treating a cell proliferative disease associated with hedgehog signaling in a subject, comprising contacting the cells with an effective amount of cyclopamine tartrate or analogues thereof, of formula:

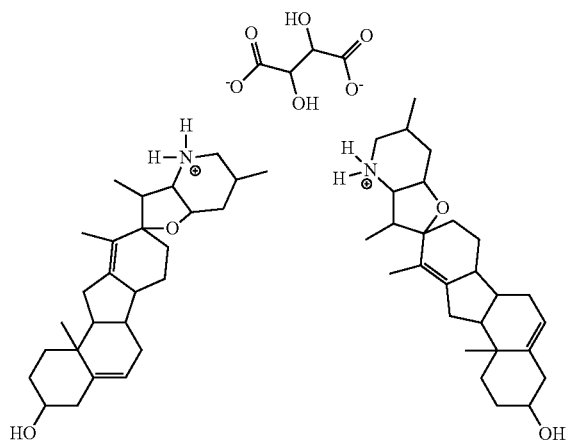

In embodiments of this invention, the proliferative disease may psoriasis, primary cancer, or a metastasized cancer. The primary cancer may be located in the head, neck, nasal cavity, paranasal sinuses, nasopharynx, oral cavity, oropharynx, larynx, hypopharynx, salivary glands, paragangliomas, pancreas, stomach, skin, esophagus, liver and biliary tree, bone, intestine, colon, rectum, ovaries, prostate, lung, breast, lymphatic system, blood, bone marrow central nervous system, or brain. The primary cancer may be basal cell carcinoma, pancreatic cancer, prostate cancer, sarcoma, lymphomas, leukemia, gastric cancer, esophageal cancer, biliary cancer, colon cancer, multiple myeloma, small cell lung cancer, glioma, breast cancer, hepatocellular or medulloblastoma.

In certain embodiments of this invention, hydroxy carboxylic salt of cyclopamine or analogue thereof, is used in cancer treatment, in combination with radiation therapy or another anti-cancer chemotherapeutic agent. The hydroxy carboxylic salt of cyclopamine may be administered locally to a tumor, systemically, or administered by inhalation, oral, intravenous, sublingual, ocular, transdermal, rectal, vaginal, topical, intramuscular, intra-arterial, intrathecal, subcutaneous, buccal, or nasal methods. In certain other embodiments, the methods of the present invention may be used for reducing in a subject, the incidence of metastasis of a cancer associated with hedgehog signaling, said method comprising administering to said subject a therapeutically effective amount of a water-soluble hydroxy carboxylic salt of cyclopamine which is less toxic than cyclopamine, such as cyclopamine tartrate In certain embodiments, the method of the instant invention may be used for antagonizing the hedgehog pathway in a cell, comprising contacting a cell expressing smoothened with an effective amount of water-soluble hydroxy carboxylic salt of cyclopamine which is less toxic than cyclopamine, such as cyclopamine tartrate or analogs thereof (in vivo or in vitro).

In one preferred embodiment, the present invention relates to a method of treating a skin tumor in a subject, comprising administering to said subject a therapeutically effective amount of cyclopamine tartrate or analogues thereof, wherein said administration results in the shrinkage of tumors on the skin.

In certain embodiments, a method of the instant invention is directed to reducing the incidence of pancreatic cancer metastasis, comprising administering to a subject in need thereof a therapeutically effective amount of cyclopamine tartrate or analogues thereof, wherein said administration inhibits metastasis of pancreatic cancers.

Hedgehog Signaling Pathway

Hedgehog signaling is essential in many stages of development, especially in formation of left-right symmetry. Loss or reduction of hedgehog signaling leads to multiple developmental deficits and malformations, one of the most striking of which is cyclopia.

Many tumors and cell proliferative diseases such as psoriasis, primary cancers, and metastatic cancers have been shown to depend on the hedgehog pathway. The growth of such cells and survival can be affected by treatment with the compounds of the present invention. It has been reported that activating hedgehog pathway mutations occur in sporadic basal cell carcinoma and primitive neuroectodermal tumors of the central nervous system. Uncontrolled activation of the hedgehog pathway has also been seen in numerous primary cancers, such as GI tract cancers including pancreatic, esophageal, gastric cancer, lung cancer, breast cancer and hepatocellular cancer.

Small molecule inhibition of the hedgehog pathway has been shown to inhibit the growth of primary cancers such as basal cell carcinoma (9), medulloblastoma (10), pancreatic cancer (11), gastrointestinal cancers, esophageal cancer (10), lung cancer (11), and prostate cancer (12, 13).

In addition, it has been shown that many primary cancer types have uncontrolled activation of the hedgehog pathway, for example, breast cancer, heptacellular cancer, hematological malignancies, basal cell carcinoma, medulloblastoma, and gastric cancer. As shown in the Example, the compound disclosed herein (cyclopamine tartrate) modulates the hedgehog pathway inhibits tumor growth. Therefore compounds are useful to treat a variety of cell proliferative diseases and conditions, such as various primary and metastatic cancers, and psoriasis.

Cyclopamine

Cyclopamine, a plant-derived steroidal alkaloid, binds directly to the transmembrane helices of SMO and inhibits hedgehog signaling. The discovery of small molecule antagonists of SMO such as cyclopamine has opened up new prospects for molecularly targeted therapy and prevention for human cancers associated with hedgehog signaling.

Oral cyclopamine can block the growth of UV-induced basal cell carcinoma cells in Ptch1+/− mice by 50%, perhaps by increasing Fas-induced apoptosis (14). Furthermore, cyclopamine treatment in this mouse model prevents formation of additional microscopic basal cell carcinoma cells, implying a potential use of cyclopamine for basal cell carcinoma prevention. Cyclopamine administration reduced basal cell carcinoma cells highlighting the specificity of cyclopamine for the hedgehog pathway. Using murine basal cell carcinoma cell lines derived from this mouse model, cyclopamine is shown to inhibit cell proliferation. Similarly, cyclopamine is effective in reducing medulloblastoma development in Ptch1+/− mice (15) as well as tumor growth of many cancer cell lines in nu/nu mice. However, there are several undesirable issues associated with cyclopamine. Cyclopamine is not water-soluble, thus drug delivery becomes a problem. Additionally, cyclopamine is toxic, causing off-target effects. Herein is provided evidence that cyclopamine derivatives specifically hydroxy carboxylic salts of cyclopamine are highly water soluble, considerably less toxic, and are effective in inhibiting hedgehog signaling and stem cell functions.

Pharmaceutical Compositions

In certain embodiments, the present invention provides pharmaceutically acceptable compositions which comprise a therapeutically-effective amount of one or more of the compounds described above, formulated together with one or more pharmaceutically acceptable carriers (additives) and/or diluents. The pharmaceutical compositions of the present invention may be specially formulated for administration in solid or liquid form, including those adapted for the following: (a) oral administration, for example, drenches (aqueous or non-aqueous solutions or suspensions), tablets, e.g., those targeted for buccal, sublingual, and systemic absorption, capsules, boluses, powders, granules, pastes for application to the tongue; (b) parenteral administration, for example, by subcutaneous, intramuscular, intravenous or epidural injection as, for example, a sterile solution or suspension, or sustained-release formulation; (c) topical application, for example, as a cream, ointment, or a controlled-release patch or spray applied to the skin; (d) intravaginally or intrarectally, for example, as a pessary, cream or foam; (e) sublingually; (f) ocularly; (g) transdermally; (h) pulmonarily, or (i) nasally.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, dispersing agents, lubricants, and/or antioxidants. Prevention of the action of microorganisms upon the compounds of the present invention may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

When the compounds of the present invention are administered as pharmaceuticals, to humans and animals, they can be given per se or as a pharmaceutical composition containing, for example, about 0.1 to 99%, or about 10 to 50%, or about 10 to 40%, or about 10 to 30, or about 10 to 20%, or about 10 to 15% of active ingredient in combination with a pharmaceutically acceptable carrier.

Actual dosage levels of the active ingredients in the pharmaceutical compositions of the present invention may be varied so as to obtain an amount of the active ingredient that is effective in achieving the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound of the invention will be that amount of the compound that is the lowest dose effective to produce a therapeutic effect. Such an effective dose will generally depend upon the factors described above. Generally, oral, intravenous and subcutaneous doses of the compounds of the present invention for a patient, when used for the indicated effects, will range from about 0.0001 to about 100 mg, or about 0.001 to about 100 mg, or about 0.01 to about 100 mg, or about 0.1 to about 100 mg per, or about 1 to about 50 mg per kilogram of body weight per day.

The subject receiving this treatment is any animal in need, including primates, in particular humans, and other mammals such as equines, cattle, swine and sheep; and poultry and pets in general.

EXAMPLE 1

Production of Cyclopamine Tartrate

Cyclopamine tartrate salt is a compound of formula:

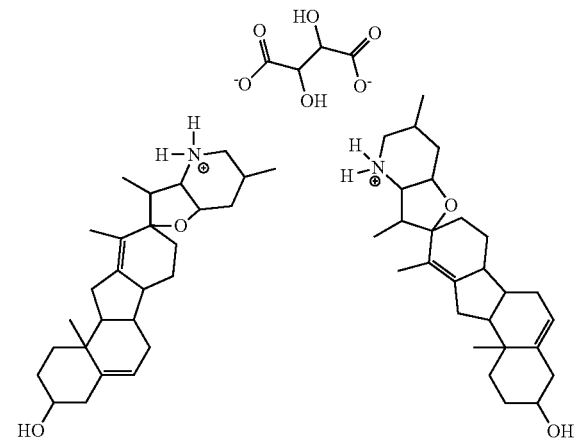

Cyclopamine tartrate is prepared by reacting 0.1 moles of tartaric acid and 0.2 moles of cyclopamine in methanol. The solution is heated till volume of the solution decreases to one third and diethyl ether is added. The solution is then cooled, filtered and precipitated. This method is further applicable to the production of any hydroxy carboxylic salts of cyclopamine in general.

EXAMPLE 2

Properties of Cyclopamine Tartrate

The toxicity and the plasma half life of cyclopamine tartrate were examined. In comparison with cyclopamine, cyclopamine tartrate was found to be soluble in water, less toxic (high tolerance 62.5 for cyclopamine tartrate vs 43.5 for cyclopamine) and has a longer half life in plasma (Table 1). With this information, the efficacy of cyclopamine tartrate for cancer treatment was tested.

TABLE 1

Properties of cyclopamine tartrate (cyc-T)

|  | Cyclopamine | Cyclopamine tartrate |
| --- | --- | --- |
| Solubility in $H_2O$ (mg/ml) | 0 | 5-10 mg/ml |
| MTD (mg/kg body weight) | 43.5 | 62.5 |
| Plasma half life time (hr) | 4.3 | 3.6-7.8 |

Effectiveness of Cyclopamine-Tartrate on Skin Tumor Shrinkage

Figure 2:
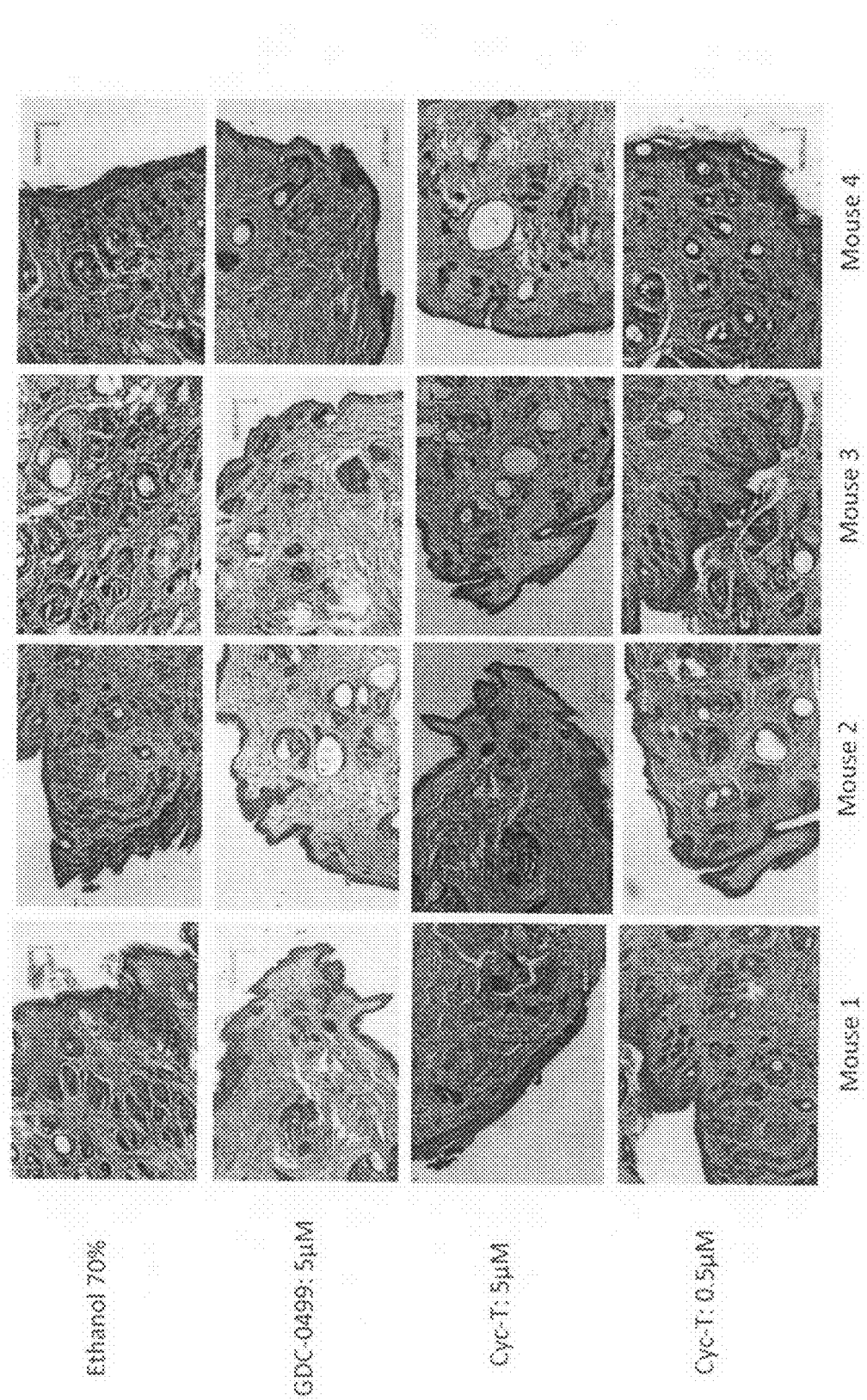
FIG. 2 depicts effectiveness of cyclopamine-tartrate on skin tumor shrinkage. Tumor area in given tissue areas (FIG. 2) examined after mice were sacrificed after 21 days of topical application of cyclopamine tartrate (cyc-T) or a known Hh signaling inhibitor GDC-0499.
Figure 3:
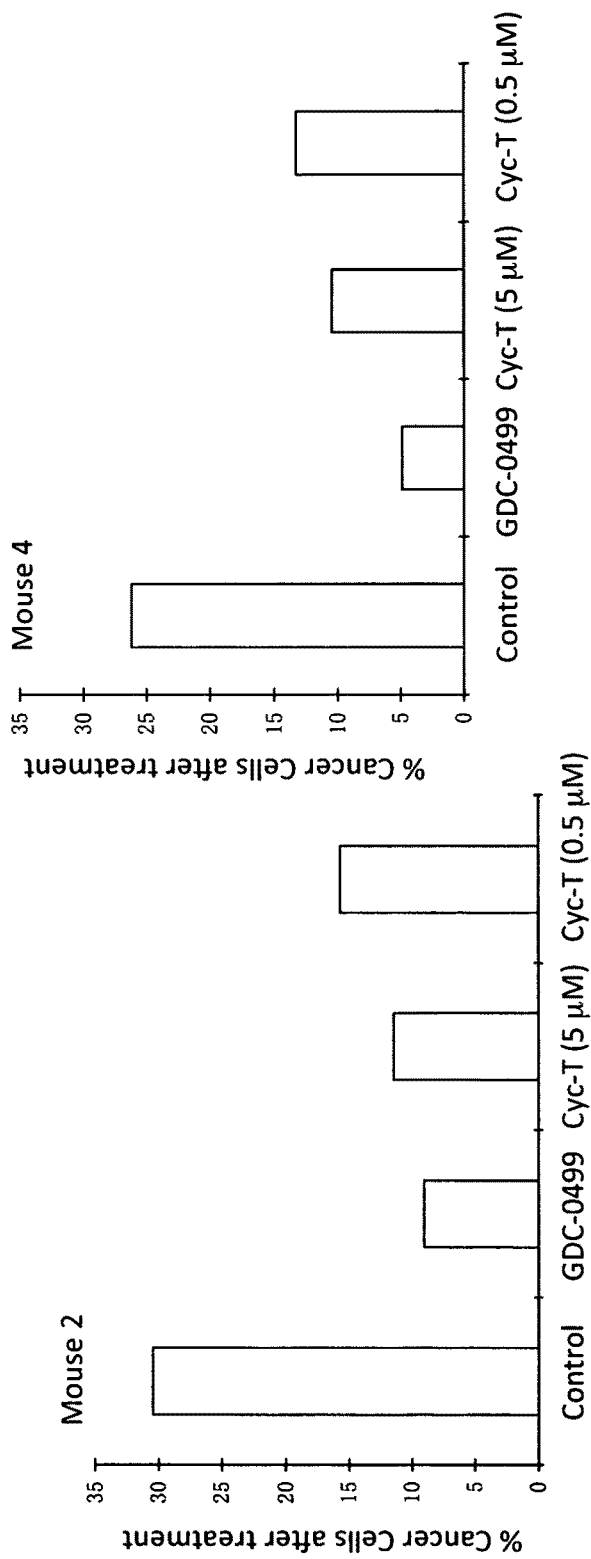
FIG. 3 depicts effectiveness of different compounds for the treatment of cancers associated with hedgehog signaling. The effect of ethanol control; GDC-0499; 5 mM cyc-T; and 0.5 mM on cancers associated with hedgehog signaling is studied, and the percentage of cancer cells surviving after treatment is shown.

In the mouse model (FIG. 2), the tumor suppressor gene Ptch1 was knocked out in the skin using keratin 14 promoter, resulting in activation of hedgehog signaling activation and development of multiple microscopic basal cell carcinomas (BCC) (mouse 1, 2 &3). Similarly, Keratin 14 promoter-driven expression of oncogene SmoM2-YFP was established, leading to activated Hh signaling and tumor development (also BCCs). After topical application of cyclopamine tartrate (cyc-T) or a known Hh signaling inhibitor GDC-0499 for 21 days, the mice were sacrificed and tumor areas in given tissue areas were examined. Quantitative analysis was performed to calculate the percentage of tumor area in a given tissue area. Eight areas were used to measure the average value from each group, which was compared for the efficacy of the drugs. The comparison illustrated in FIG. 3 demonstrates that Cyc-T is a very effective inhibitor for hedgehog signaling-mediated tumors.

EXAMPLE 3

Orthotopic Mouse Model for Cancer Metastasis

Figure 4:
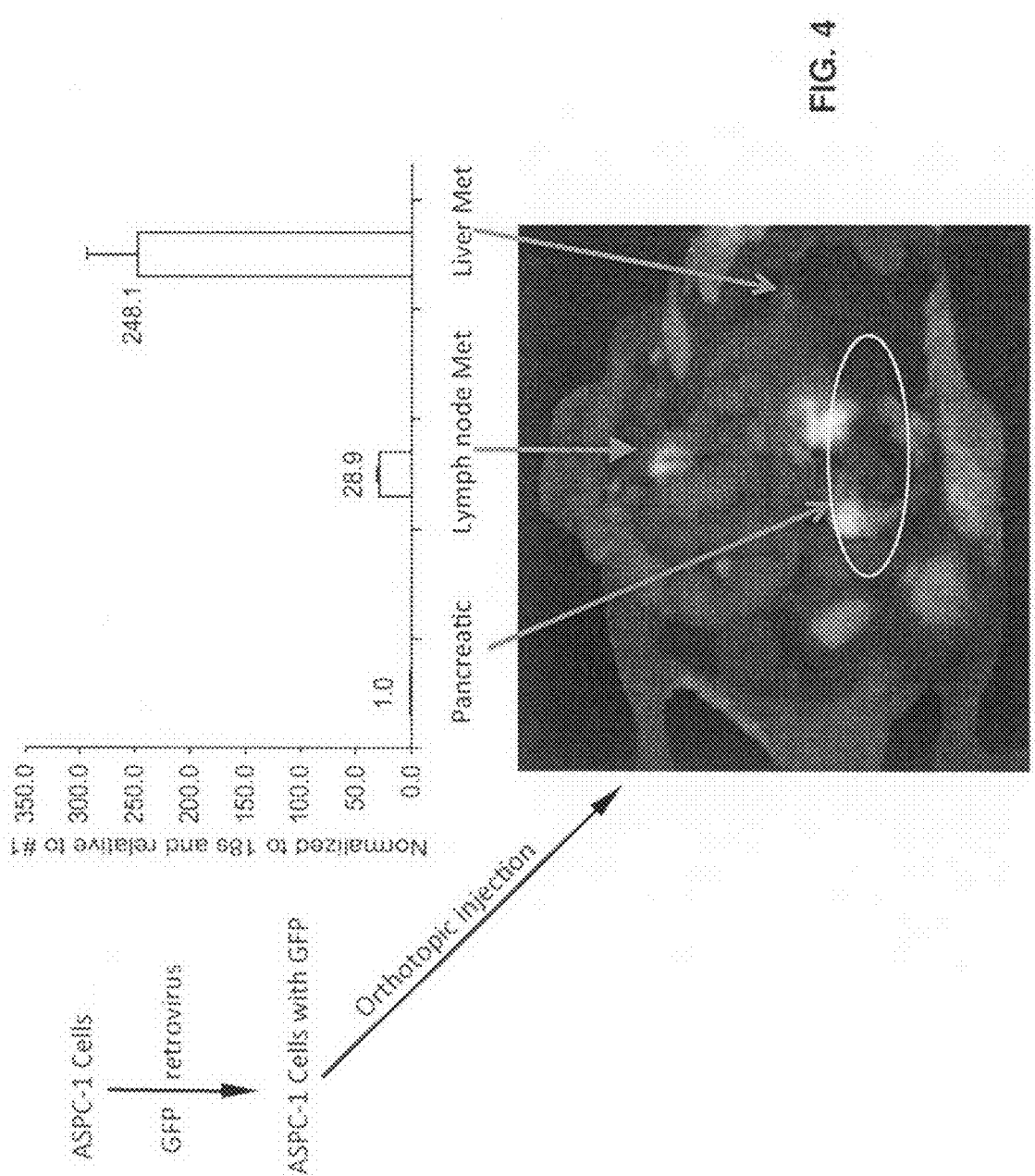
FIG. 4 shows an orthotopic mouse model for pancreatic cancer metastasis. Green flourescent protein (GFP) was expressed in pancreatic cancer cell line ASPC-1, then injected into pancreas of nude mice and 6-8 weeks later, GFP expression was observed in pancreas, lymph nude and liver. Gene expression analysis of human hedgehog target gene Gli1 showed an increased expression of Hh target gene in lymph node and liver, indicating that Hh signaling is activated during pancreatic cancer metastasis.

An orthotopic mouse model for pancreatic cancer metastasis was established to test the effect of Cyc-T on pancreatic cancer. Green flourescent protein (GFP) was expressed in pancreatic cancer cell line ASPC-1, and then injected into pancreas of nude mice. 6-8 weeks later, GFP expression was observed in pancreas, lymph nude and liver (FIG. 4). Gene expression analysis of human hedgehog target gene Gli1 showed an increased expression of Hh target gene in lymph node and liver, indicating that Hh signaling is activated during pancreatic cancer metastasis (FIG. 4).

Effect of Cyc-T on Mouse Model for Cancer Metastasis

Figure 5:
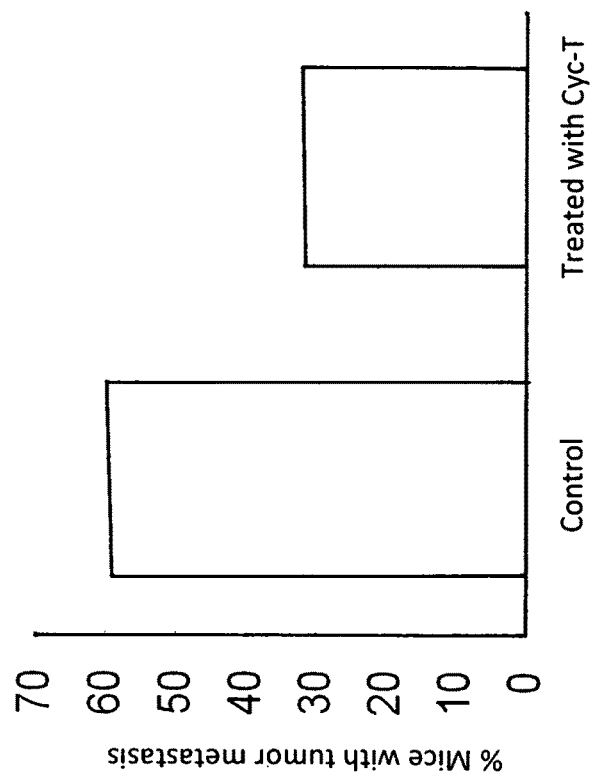
FIG. 5 shows the effect of Cyc-T on pancreatic cancer metastasis. Mice were treated with solvent (saline) or Cyc-T. Tumor metastasis was more prevalent in the control group was more frequent than in the mice treated with Cyc-T (60% vs. 32%), indicating that Cyc-T reduces tumor metastasis of pancreatic cancer.

The effect of cyc-T was tested in the mouse model for pancreatic cancer metastasis described supra. Of the 40 mice with pancreatic cancer model, 20 were treated with solvent (saline) and the other 20 were treated with Cyc-T. Mice in the control group displayed more frequent tumor metastasis than those treated with Cyc-T (60% vs. 32%), indicating that Cyc-T reduces tumor metastasis of cancer (FIG. 5).

EXAMPLE 4

Inhibition of Hedgehog Signaling and Stem Cell Functioning

Figures 6A, 6B:
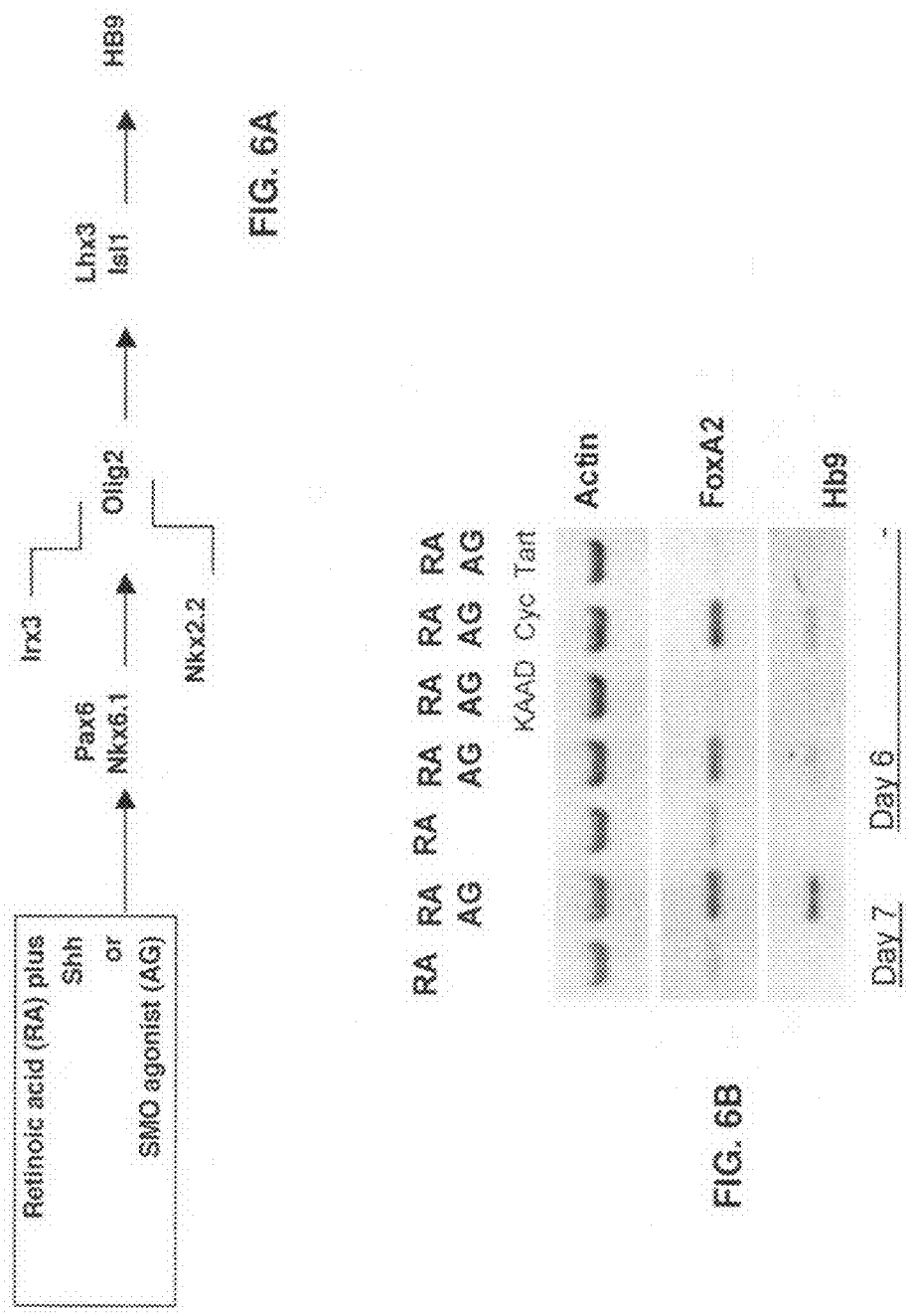
FIGS. 6A-6D depict Inhibition of hedgehog signaling, embryonic body formation and motor neuron differentiation by cyclopamine tartrate salt. KAAD—KAAD cyclopamine; Cyc—cyclopamine; Tart—cyclopamine tartarate salt; Cyc-T: cyclopamine tartarate salt.
Figure 6C:
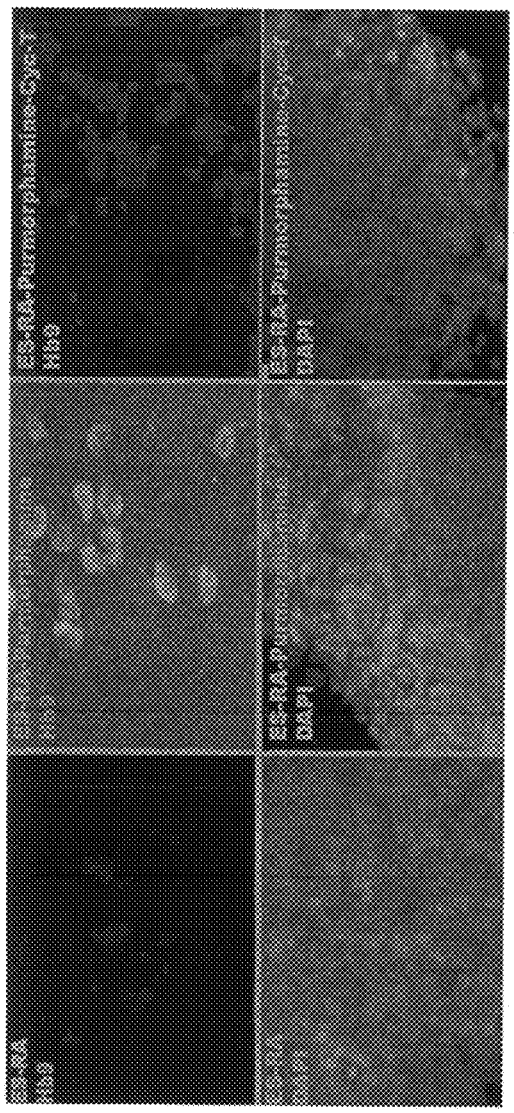
Figure 6D:
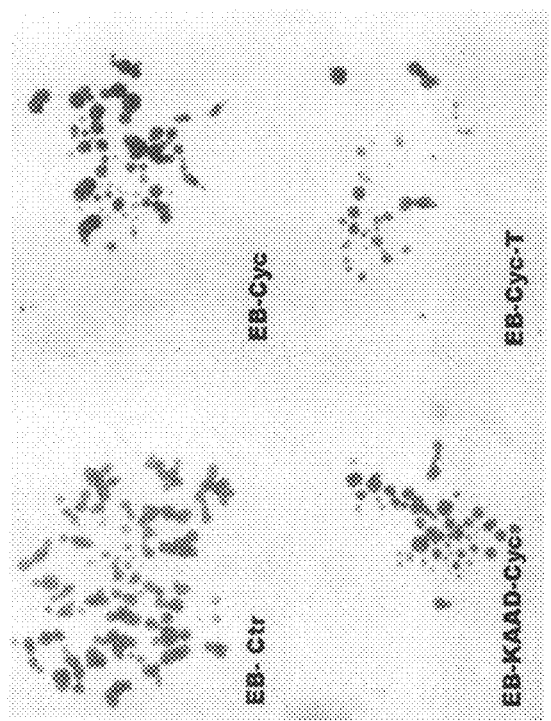

Cyclopamine tartrate salt is effective in inhibit hedgehog signaling and stem cell functions. To test stem cell functions, motor neuron differentiation experiments were used. First embryonic stem cells were used to form stem cell sphere (embryonic bodies, EB). In the presence of retinoic acid (RA) and sonic hedgehog or SMO agonist purmorphamine (AG), several types of neurons can be differentiated. These neurons can be distinguished by distinct markers. Hb9 is regarded as a marker for motor neuron (FIG. 6A). As can be seen in FIGS. 6B-6D, cyclopamine tartrate salt is as effective as KAAD-cyclopamine, one of the most potent hedgehog signaling inhibitor (FIGS. 6B, 6D), indicating cyclopamine tartrate is a potent hedgehog signaling inhibitor.

The following references are cited herein:
1. Nusslein-Volhard, C. & Wieschaus, E. 1980. Nature 287, 795-801.
2. Sasaki, Hui, Nakafuku & Kondoh, 1997. Development 124, 1313-22.
3. Kinzler, K. W. & Vogelstein, B. 1990. Mol Cell Biol 10, 634-42.
4. Hahn, H. et al. 1996. Cell 85, 841-51.
5. Johnson, R. L. et al. 1996. Science 272, 1668-71.
6. Epstein, E., Jr. 2001. Med Pediatr Oncol 36, 555-8.
7. Xie, J. 2008. Acta Biochim Biophys Sin (Shanghai) 40, 670-80.
8. Chen, Taipale, Cooper, & Beachy, 2002. Genes Dev 16, 2743-8.
9. Williams, et al. 2003. PNAS 100, 4616-21.
10. Berman, et al. 2002 Science 297, 1559-61.
11. Berman, et al. 2003 Nature 425, 846-51.
12. Watkins, et al. 2003. Nature 422, 313-7.
13. Karhadkar, et al. 2004. Nature 431, 707-12.
14. Athar M, Li C, et al. 2004. Cancer Res 64, 7545-52.
15. Sanchez P, et al. 2005. Mech Dev, 122, 223-230.

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A method of treating a subject having metastatic cancer with a hyperactive hedgehog pathway comprising administering to the subject having metastatic cancer an effective amount of cyclopamine tartrate.

2. The method of claim 1, wherein the metastasis is pancreatic cancer metastasis.

3. The method of claim 1, further comprising administering radiation therapy or another anti-cancer chemotherapeutic agent.

4. The method of claim 1, wherein the cyclopamine tartrate is administered locally to a tumor.

5. The method of claim 1, wherein the cyclopamine tartrate is administered systemically.

* * * * *